United States Patent [19]

Yabe et al.

[11] Patent Number: 5,536,236
[45] Date of Patent: Jul. 16, 1996

[54] COVERED ENDOSCOPE SYSTEM

[75] Inventors: Hisao Yabe, Hachioji; Yoshihiro Iida, Tama; Akira Suzuki; Hideo Ito, both of Hachioji; Yoshio Tashiro, Hino; Minoru Yamazaki, Hachioji; Osamu Tamada, Hachioji; Tsutomu Ishiguro, Hachioji, all of Japan

[73] Assignee: Olympus Optical Co., Ltd., Tokyo, Japan

[21] Appl. No.: 37,336

[22] Filed: Mar. 26, 1993

[30] Foreign Application Priority Data

Feb. 12, 1993 [JP] Japan ................... 5-004272 U
Feb. 12, 1993 [JP] Japan ................... 5-004273 U
Feb. 12, 1993 [JP] Japan ................... 5-004274 U

[51] Int. Cl.⁶ .................................................. A61B 1/00
[52] U.S. Cl. ..................... 600/125; 600/121; 600/129
[58] Field of Search ........................ 128/4, 6; 600/121, 600/125, 129, 123, 124

[56] References Cited

U.S. PATENT DOCUMENTS

| Re. 34,110 | 9/1992 | Opie . | |
|---|---|---|---|
| 3,162,190 | 12/1964 | Del Gizzo . | |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,154,164 | 10/1992 | Chikama | 128/4 |
| 5,201,908 | 4/1992 | Jones | 128/4 |
| 5,237,984 | 8/1993 | Williams, III et al. | 128/4 |
| 5,257,617 | 11/1993 | Takahashi . | |

FOREIGN PATENT DOCUMENTS

| 0184778 | 6/1986 | European Pat. Off. . |
|---|---|---|
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-37030 | 2/1991 | Japan . |
| 3-37029 | 2/1991 | Japan . |
| 3-29635 | 2/1991 | Japan . |
| 3-29634 | 2/1991 | Japan . |
| 3-221024 | 9/1991 | Japan . |
| 3-101906 | 10/1991 | Japan . |
| 3-101907 | 10/1991 | Japan . |
| 3-101905 | 10/1991 | Japan . |
| 3-101904 | 10/1991 | Japan . |
| 3-101903 | 10/1991 | Japan . |
| 3-101902 | 10/1991 | Japan . |
| 3-101901 | 10/1991 | Japan . |
| 4-325138 | 11/1992 | Japan . |

Primary Examiner—Richard J. Apley
Assistant Examiner—Beverly M. Flanagan
Attorney, Agent, or Firm—Armstrong, Westerman, Hattori, McLeland & Naughton

[57] ABSTRACT

A covered endoscope system according to the present invention comprises a cover and a coverable endoscope to be inserted into the cover for use. Herein, an optical filter is mounted in the distal part of a cover abutting on the front of an observation optical system of the coverable endoscope.

4 Claims, 13 Drawing Sheets

COVERED ENDOSCOPE SYSTEM

BACKGROUND OF THE INVENTION

1. Field of the Invention

The present invention relates to a covered endoscope system in which a coverable endoscope is sheathed with a cover and a body cavity is examined.

2. Description of the Related Art

In recent years, endoscopes have been widely adopted in the fields of industries and medicine alike.

As for endoscopes employed in the field of medicine, since an endoscope is inserted into a living body, a patient's body fluid or mucus sometimes adheres to an observation window formed at the distal part of an insertional part of the endoscope and thus reduces any possibility of a thorough observation of a lesion. An endoscope system is provided with an air supply function for supplying air to blow off remaining water from the observation window and a water supply function for supplying water to clean the observation window. The air or water supply function is activated by operating an operation button formed in the proximal portion of the endoscope, and executed via an air supply channel or a water supply channel.

The endoscope has multiple channels including not only the air and water supply channels but also a suction channel and a treatment adapter channel.

By the way, an endoscope that has been used for treatment must be cleaned or disinfected immediately, so that it can be reused for the next patient. However, it is a nuisance and time-consuming to thoroughly clean and disinfect an endoscope. This constitutes a factor in the deterioration of the use efficiency of an endoscope.

A covered endoscope has recently been employed, wherein an endoscope itself is sheathed with a cover, and used for each patient. The cover with which the endoscope is sheathed is disposed of after treatment is completed. This covered endoscope permits simple cleaning and disinfection.

In the covered endoscope, only channels which must open onto a patient's body cavity are mounted on a cover. A coverable endoscope having an observing means and an illuminating means is sheathed with a cover so as to not directly touch the inside of a patient's living body.

This kind of covered endoscope has been disclosed in, for example, U.S. Pat. No. 4,646,722 or U.S. Pat. No. 3,162,190.

In case a laser treatment adaptor is used in conjunction with a covered endoscope for treatment, when a laser beam generated by the laser treatment adaptor is irradiated to a region to be treated, part of the laser beam is reflected from the region to be treated, and enters an imaging device via an observation window and an observation optical system which are mounted in the distal part of an endoscope. This damages the imaging device either physically or optically. To avoid this damage, some endoscopes are provided with an optical filter that prevents a laser beam from passing through an objective optical system of an endoscope.

A laser beam currently employed for endoscopic treatment includes, for example, a YAG laser beam, a $CO_2$ laser beam, and a KTP laser beam which have different wavelengths. A single kind of filter can cut off only a specific laser beam, which necessitates endoscopes having filters designed for respective laser beams. When an observational beam irradiated from an illumination optical system is likely to be reflected from a region to be treated and cause a halation, an endoscope having a polarizing filter must be used. Observation using infrared rays requires an endoscope having an infrared observation filter. Thus, an endoscope having a filter designed for a specific band of wavelengths or purpose of use of a beam must be employed depending on the nature of examination or treatment.

Aside from the foregoing endoscopes having various filters in the optical systems thereof, an endoscope having a streamlined hood at the distal part thereof, and an endoscope having a hood that projects by a specified distance to provide a distance between the distal part thereof and a region to be treated have been put to use.

Procuring multiple endoscopes in compliance with purposes of use has been a great financial burden to a user.

On the other hand, when a high-frequency treatment adaptor is inserted into a treatment adaptor channel of a cover and treatment is performed, a noise generated by the high-frequency treatment adaptor has an adverse effect on an imaging device placed inside the distal part of a coverable endoscope. Endoscopic images produced appear with noises on a monitor, which are, therefore, hard to see. As a countermeasure, the imaging device placed in the endoscope is provided with an electromagnetic shield. Nevertheless, it seems almost impossible to eliminate the noise perfectly.

An observation window formed at the distal part of a cover is shaped substantially like the distal part of a coverable endoscope. A patient's body fluid or mucus tends to adheres to the observation window, whenever the observation window is not dewatered soon after cleaned.

The layout of a coverable endoscope, a water supply channel, and an air supply channel, which run through a cover, has not been devised even though there have been many careful studies on the matter. Therefore, a field of view is disturbed, or the flow of fluid through fluid pipes or air pipes is disordered to eventually disrupt the air or water supply function.

Furthermore, when the observation window become cloudy, observation images appearing on the monitor become hard to see.

In the covered endoscope, an endoscope insertion channel into which a coverable endoscope is inserted is formed in an insertional part cover or one of the components of a cover. Nevertheless, a guide has not been formed in an endoscope insertion hole in a locking cap formed in the proximal portion of the insertional part cover or an inlet of an endoscope alignment hole formed at the distal part of the insertional part cover.

Therefore, when the coverable endoscope is inserted in the insertional part cover, the rigid distal part of the coverable endoscope is hooked on the locking cap or the inner circumferential surface of a distal structure. Thus, insertional smoothness is poor. When the coverable endoscope is pushed into the endoscope insertion channel forcibly, an insertional part of the coverable endoscope may be bent, an optical lens placed in the distal part of the coverable endoscope may be damaged, or the insertional part cover may be torn.

In the covered endoscope, the distal part of the coverable endoscope is fitted into the endoscope alignment hole, and thus aligned and secured. The diameter of the endoscope alignment hole is designed larger than necessary so that the distal part of the covered endoscope will be fitted into the endoscope alignment hole smoothly. Furthermore, the profile irregularity of the inner circumferential surface of the alignment hole is lowered much more than necessary so that the distal part of the coverable endoscope can be inserted into the endoscope alignment hole smoothly.

Consequently, only a low frictional resistance is present between the endoscope alignment hole and the distal part of the coverable endoscope. When endoscopic examination is conducted in this state, if bending is performed, the distal part of the coverable endoscope may sometimes be displaced from the endoscope alignment hole.

SUMMARY OF THE INVENTION

An object of the present invention is to provide a covered endoscope system having a cover capable of coping with a purpose of use of a treatment adaptor to be inserted into a treatment adaptor channel of a cover during an endoscopic examination.

Another object of the present invention is to provide a covered endoscope system in which an air supply channel, a water supply channel, and a coverable endoscope, which are mounted in a cover, are laid out functionally to eventually offer improved workability.

Yet another object of the present invention is to provide a covered endoscope system capable of offering upgraded smoothness in inserting the distal part of a coverable endoscope into an endoscope insertion hole or an endoscope alignment hole, and of eliminating displacement of the distal part of the coverable endoscope fitted into the endoscope alignment hole.

Briefly, a covered endoscope system according to the present invention comprises a cover and a coverable endoscope to be inserted into the cover for use, wherein an optical filter is mounted in the distal part of the cover abutting on the front of an observation optical system of the coverable endoscope.

The other features and advantages of the present invention will be apparent from the description below.

BRIEF DESCRIPTION OF THE DRAWINGS

FIG. 1 is an oblique view for explaining a configuration of a covered endoscope system;

FIG. 2 is a plan view for explaining a construction of a coverable endoscope;

FIG. 3 is a plan view showing an operational part and an angulation unit:

FIG. 4 is a cross-sectional view showing a cover in which a coverable endoscope is inserted;

FIG. 5 is a cross-sectional view showing channels in a distal structure;

FIG. 6 is a front view of a distal structure;

FIG. 7 is a front view showing other example of a distal structure;

FIG. 8 is a front view showing a distal structure having an observation window on which a dewatering means is formed;

FIG. 9 is an oblique view of an observation window;

FIG. 10 shows a B—B cross section of the observation window of FIG. 8;

FIG. 11 is a front view of a distal structure having an observation window on which other dewatering means is formed;

FIG. 12 is a cross-sectional view showing an observation window of a distal structure and a distal part of a coverable endoscope;

FIG. 13 is an oblique view showing a lens of an observation optical system and a heating coil thereof;

FIG. 14 is an oblique view showing an observation window and a heating coil;

FIG. 15 is a cross-sectional view showing an insertional part cover and a coverable endoscope;

FIG. 16 is an enlarged view showing the shape of a guide;

FIG. 17 is an enlarged view showing other shape of a guide;

FIG. 18 is an oblique view showing a guide formed at a distal part of a coverable endoscope;

FIG. 19 is a cross-sectional view showing a coverable endoscope tightly fitted into an endoscope alignment hole;

FIG. 20 is an A—A cross-sectional view of the distal structure shown in FIG. 19 and an oblique view showing an alignment holding means;

FIG. 21 is an A—A cross-sectional view of the distal structure shown in FIG. 19 and an oblique view showing other example of an alignment holding means;

FIG. 22 is an A—A cross-sectional view of the distal structure shown in FIG. 19 and an oblique view showing a distal part of a coverable endoscope;

FIG. 23 is an oblique view showing a treatment adaptor channel with a shielding means;

FIG. 24 is a cross-sectional view showing a state that a coverable endoscope is fitted into and held by an insertional part cover in which a treatment adaptor channel with a shielding means is mounted;

FIG. 25 is an oblique view of a terminal;

FIG. 26 is a cross-sectional view of a terminal;

FIG. 27 is an oblique view showing a treatment adaptor channel with other shielding means;

FIG. 28 is a cross-sectional view showing a state that a coverable endoscope is fitted into and held by an insertional part cover in which a treatment adaptor channel with other shielding means is mounted;

FIG. 30 is a cross-sectional view of a distal structure with a cuff;

FIG. 31 is a cross-sectional view of a distal structure on which an insertional smoothness improving means is formed;

FIG. 33 is an oblique view showing a mouthpiece-united insertional part cover;

FIG. 34 is an oblique view showing other example of a mouthpiece-united insertional part cover;

FIG. 35 is an oblique view showing the other example of a mouthpiece-united insertional part cover;

FIG. 36 is an oblique view showing another example of a mouthpiece-united insertional part cover;

FIG. 37 is a cross-sectional view showing a mouthpiece rolling means; and

FIG. 38 is a cross-sectional view showing other example of a mouthpiece rolling means.

DETAILED DESCRIPTION OF THE PREFERRED EMBODIMENTS

Referring to FIGS. 1 to 4, the first embodiment of the present invention will be described.

Figure 1:
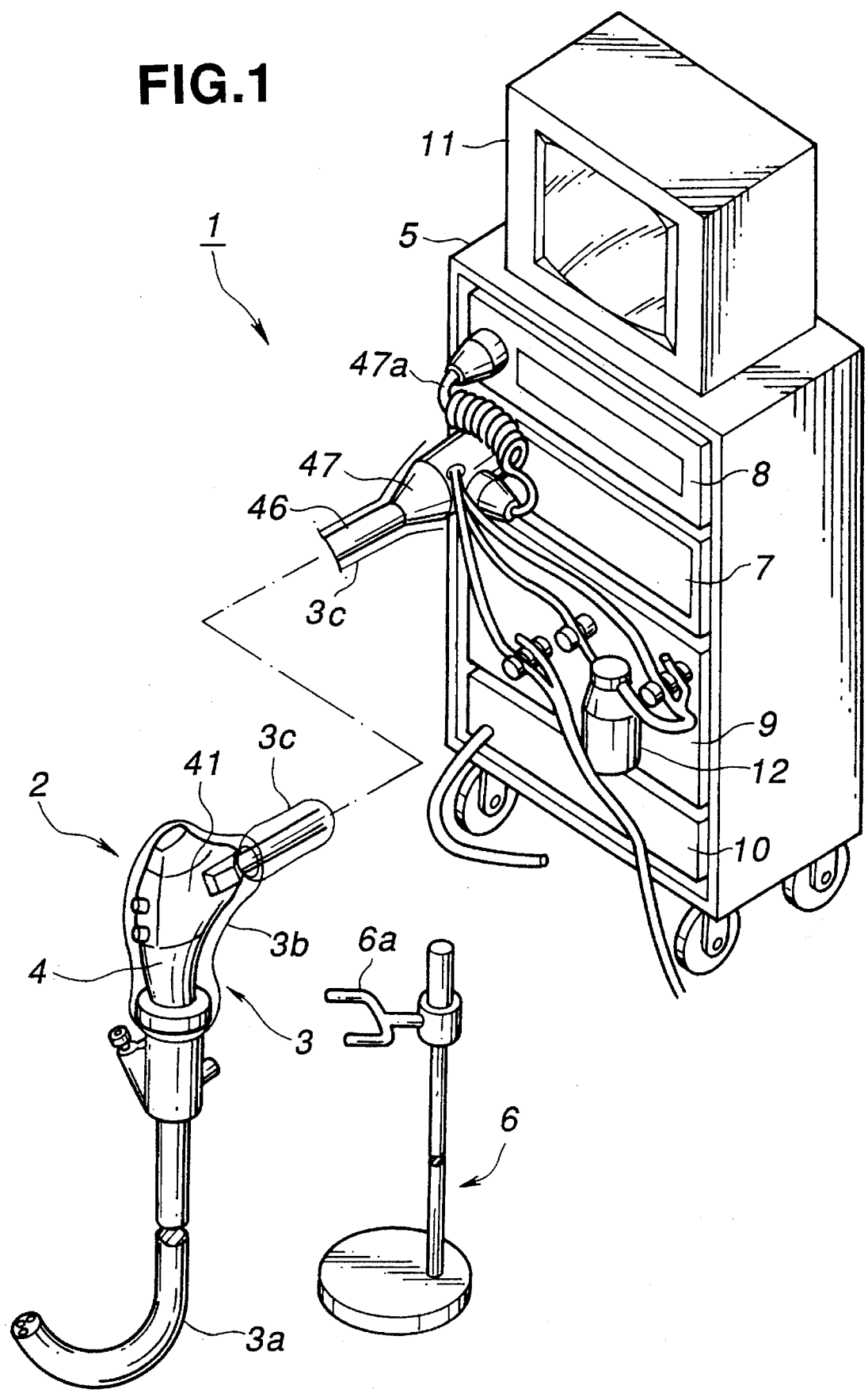
FIGS. 1 to 4 show the first embodiment of the present invention.

As shown in FIG. 1, a covered endoscope system 1 has a channeled covered endoscope (hereafter, covered endoscope) 2. The covered endoscope 2 consists mainly of a cover 3 and a coverable endoscope 4.

Figure 2:
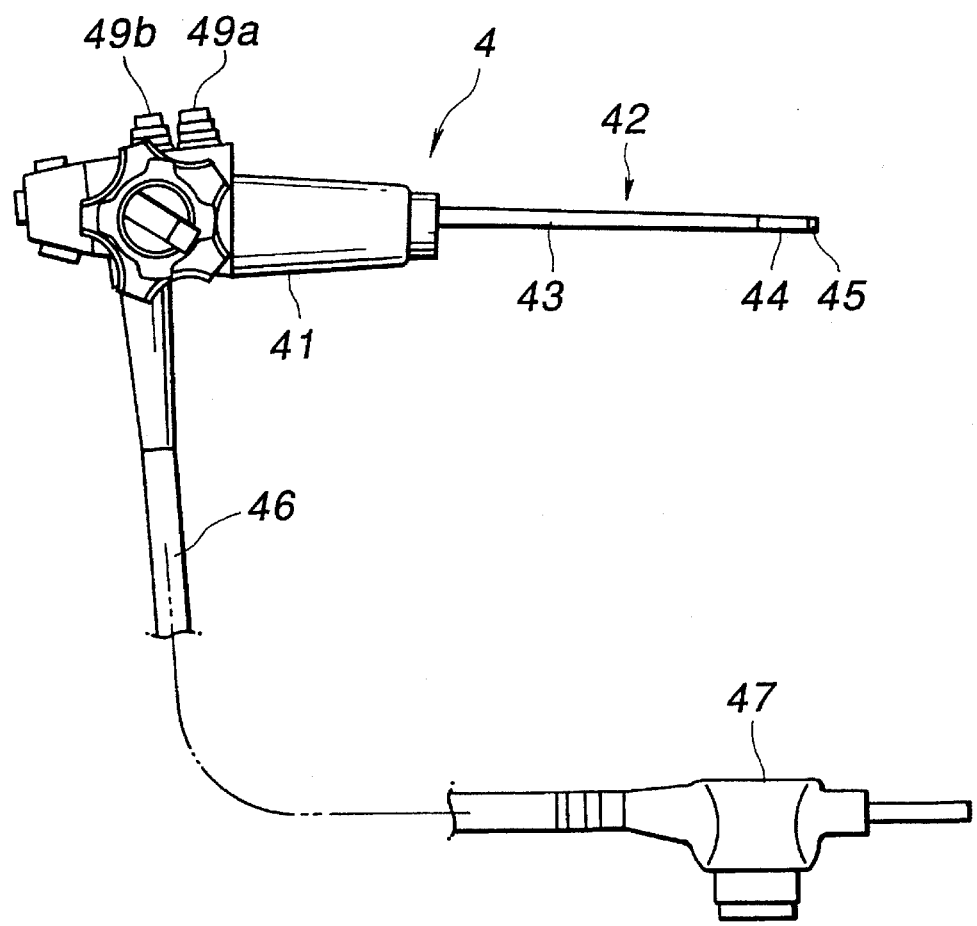

As shown in FIG. 2, the coverable endoscope 4 is an electronic endoscope, wherein an elongated insertional part 42, which is inserted into a body cavity, extends from the front of an operational part 41 that is formed in the proximal portion of the coverable endoscope and also serves as a grip. The insertional part 42 has a flexible tube 43 as a main component. A bending section 44 capable of bending vertically and laterally is coupled with the distal end of the flexible tube 43. A rigid distal part 45 is extending from the front of the flexible tube 43.

A universal cord 46 containing, for example, a signal cable and a light guide fiber bundle which are not shown are extending from the side of the operational part 41. The universal cord 46 is connected to a light source apparatus and a video processor, which will be described later, via a connector 47 attached to the distal part thereof.

Figure 3:
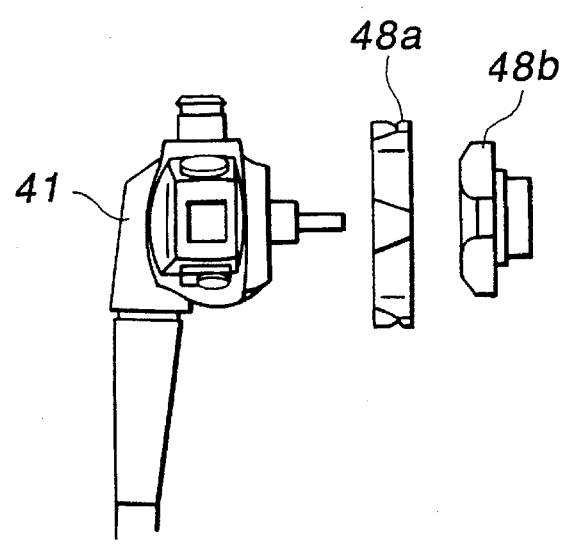

As shown in FIG. 3, angulation knobs 48a and 48b for angling the bending section 44 are attached to the operational part 41 so as to be freely detachable. In addition, an air/water supply control switch 49a, a suction control switch 49b, and various function switches for photography 49c are arranged on the operational part 41.

As shown in FIG. 1, a cover 3 comprises an insertional part cover 3a for shielding the insertional part 42 of the coverable endoscope 4, an operational part cover 3b for shielding the operational part 41 of the coverable endoscope, and a universal cord cover 3c for shielding the universal cord 46 of the coverable endoscope 4. When sheathed with these covers 3a, 3b, and 3c in such a manner that water will be shut out tightly, the coverable endoscope 4 becomes usable for examination.

The covered endoscope system 1 includes a cart 5 accommodating various peripheral equipment connected to the coverable endoscope 2, and a cover holding instrument 6 for holding the coverable endoscope 2.

As illustrated, the cart 5 accommodates various peripheral equipment; such as, a light source apparatus 7, a video processor 8, a fluid control apparatus 9, and a cover dilator (hereafter, dilator) 10. A monitor 11 for displaying endoscopic images is placed on the top plate of the cart 5.

When the coverable endoscope 4 is connected to the light source apparatus 7 via a connector 47, illumination light is supplied to the distal part of the endoscope.

When linked with the connector 47 of the coverable endoscope 4 via connection cable 47a, the video processor 8 converts electric signals sent from the endoscope into standard video signals so that endoscopic images will be displayed on the monitor 11.

The fluid control apparatus 9 supplies air or water via a channel, which will be described later, mounted in the cover. When a water supply source 12 or an air supply source which is not shown are installed, a channel linked with the air supply source or water supply source is closed or opened using, for example, an electromagnetic valve, air or water supply is carried out.

The dilator 10 feeds air to the cover 3 and thus dilates the cover 3, so that the coverable endoscope 4 can be sheathed or unsheathed smoothly.

When the coverable endoscope 4 is inserted into the insertional part cover 3a, an arm 6a of the cover holding instrument 6 holds a cap, which will be described later, of the insertional part cover 3a. The use of the cover holding instrument 6 enables the holding of the coverable endoscope 4 without causing a hand to touch the cover 3 directly. Thus, hygiene is ensured and workability is upgraded.

Figure 4:
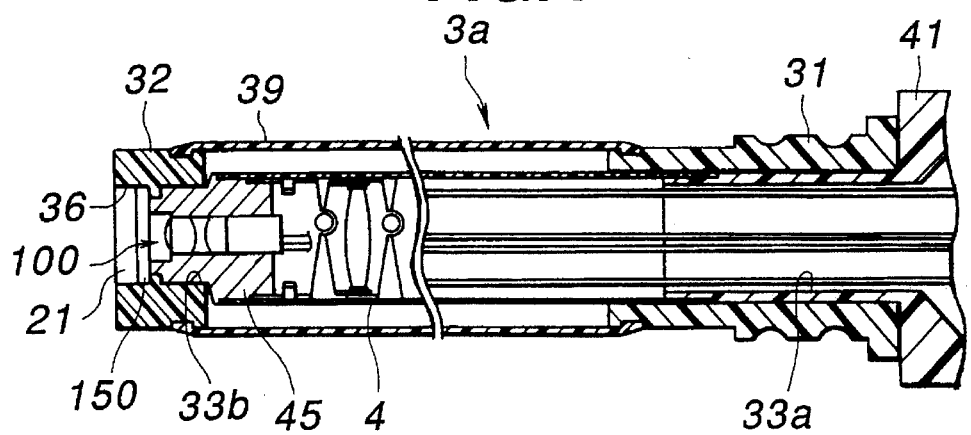

As shown in FIG. 4, the distal part 45 of the coverable endoscope 4 having an observation optical system 100 is fitted into an endoscope alignment hole 33b formed in a distal structure 32 of the insertional part cover 3a.

As illustrated, the insertional part cover 3a is made by coupling an operational endoscope part locking cap (hereafter, locking cap) 31 formed at the proximal end thereof with the distal structure 32 formed at the distal end thereof using a flexible elongated cover skin 39 airtightly.

A coverable endoscope insertion hole 33a is bored through the locking cap 31 in the axial direction thereof in such a manner that the insertional part 42 of the coverable endoscope 4 will be tightly fitted into the coverable endoscope insertion hole 33a.

A lens hole 36 in which an observation window 21 is locked is bored on the distal surface of the distal structure 32 in the axial direction thereof, and an endoscope alignment hole 33b into which the distal part 45 of the coverable endoscope 4 is fitted tightly is formed behind the distal surface of the distal structure 32 in the axial direction thereof.

The lens hole 36 of the distal structure 32 of the insertional part cover 3a has the observation window 21 coated with a film-type optical filter 150. When the distal part 45 of the coverable endoscope 4 is locked in the endoscope alignment hole 33b, the observation optical system 100 of the coverable endoscope 4 is aligned with the observation window 21 in a specified manner. The optical filter may be coated over either the outer or inner surface alone of the observation window 21, or both of the surfaces.

The optical filter 150 to be coated over the observation window 21 includes a film-type filter that does not pass various laser beams such as a YAG laser beam, $CO_2$ laser beam, and KTP laser beam, an optical filter that can cut off or pass a specified wavelength, an ND filter, a color compensation filter, a polarizing observation filter, and a fluorescent observation filter, which cope with different purposes of use.

The operation of the covered endoscope system having the aforesaid configuration will be described.

When a YAG laser is used as a treatment adaptor in conjunction with an endoscope, an operator selects the cover 3 having the observation window 21 coated with a film-type filter that does not pass a YAG laser beam, and sheathes the coverable endoscope 4 with the cover 3. The operator then inserts the covered endoscope 2 into a body cavity, and manipulates the laser while monitoring endoscopic images.

The observation window 21 coated with the film-type filter 150 that does not pass a YAG laser beam is abutting on the front of the observation optical system 100 of the coverable endoscope 4. Endoscopic images of a region to be observed can, therefore, be monitored without influence of the YAG laser beam.

As described above, when the cover 3 whose observation window 21 is placed in the distal structure 32 of the insertional part cover 3a and coated with the film-type filter 150 in conformity with a purpose of treatment or observation is made available in various types, an operator can select the cover 3 most suitable for his/her purpose of use.

The film-type filter 150 coated over the observation window 21 prevents a laser beam from entering the observation optical system 100. Therefore, an imaging device placed in the coverable endoscope 4 will not be damaged.

Furthermore, it becomes unnecessary to procure a plurality of expensive endoscopes that are constructed exclusively for respective purposes, which results in cost saving and leads to hygienic and efficient examination and treatment.

The filter may be made available in the form of a plate independent of the observation window 21 in various types, and interposed between the observation window 21 of the insertional part cover 3a and the observation optical system 100 of the coverable endoscope 4. When a filter plate is abutted on the front of the observation optical system using a simple locking means, use without contamination can be achieved and care need not be taken that the filter may fall into a body cavity.

Figure 5:
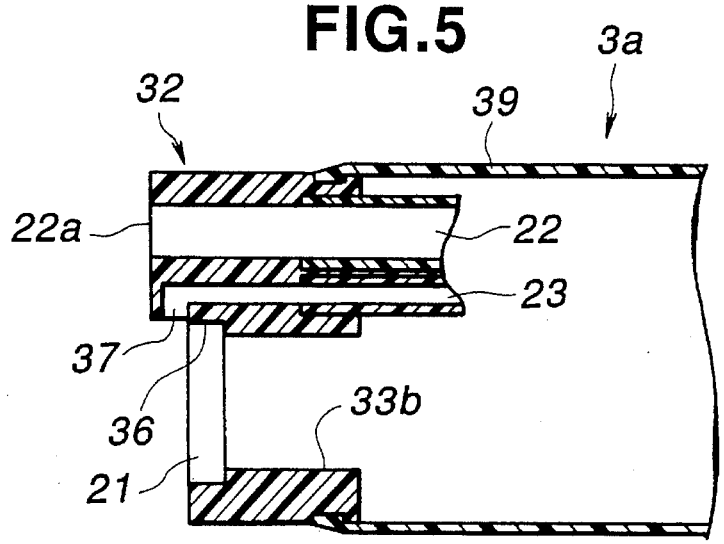
FIGS. 5 to 7 show the second embodiment of the present invention.
Figure 6:
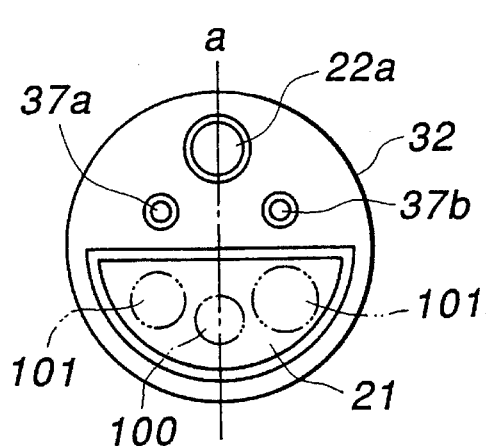
Figure 7:
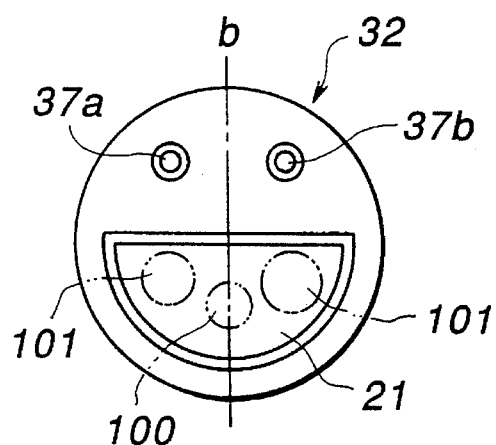

Referring to FIGS. 5 to 7, the second embodiment of the present invention will be described.

As shown in FIG. 5, a treatment adaptor channel hole 34b and an air/water supply hole 35b, with which a treatment adaptor channel 2 that is realized with a flexible tube running through an insertional part cover 3a and serves as a suction channel, and an air/water supply channel 23 are joined, are formed in a distal structure 32. The distal structure 32 has a treatment adaptor channel outlet 22a, an air nozzle 37a, and a water nozzle 37b, which are exits of the treatment adaptor channel hole 34b and air/water supply hole 35b.

As shown in FIG. 6, an illumination optical system 101 of a coverable endoscope 4, the treatment adaptor channel outlet 22a, air nozzle 37a, and water nozzle 37b are arranged so as to be substantially symmetrical with respect to a substantial center line, a, passing through a substantial center of the observation optical system 100 of the coverable endoscope 4 that is fitted into an endoscope alignment hole 33b.

Since the exits and an optical system are thus arranged in the distal structure 32 of the insertional part cover 3a to have a substantially symmetrical positional relationship with the center line a, the position of the endoscope agrees with the position of an observed image. This improves observational performance and treatment efficiency. The operation and advantages are identical to those of the first embodiment.

In the insertional part cover 3a, shown in FIG. 7, which does not have the treatment adaptor channel hole 22a, the air nozzle 37a and water nozzle 37b are arranged so as to be substantially symmetrical with respect to a substantial center line, b, passing through a substantial center of the observation optical system 100.

Referring to FIGS. 8 to 11, the third embodiment of the present invention will be described.

An observation window 21 mounted in a distal structure 32 of an insertional part cover 3a is much larger than an observation window of an endoscope that is larger in appearance than a coverable endoscope and used without a cover. Therefore, after body fluid which has adhered to the observation window 21 in a body cavity is washed away, the observation window 21 is not promptly dewatered. Consequently, endoscopic observation images become hard to see. To overcome this drawback, the observation window 21 in the present embodiment is provided with a dewatering means.

Figure 8:
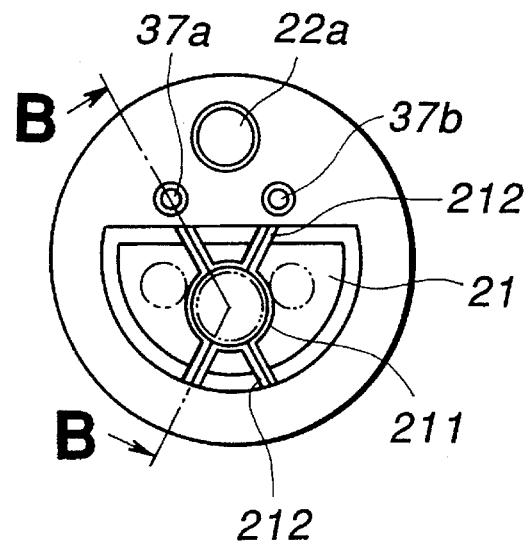
FIGS. 8 to 11 show the third embodiment of the present invention.
Figure 9:
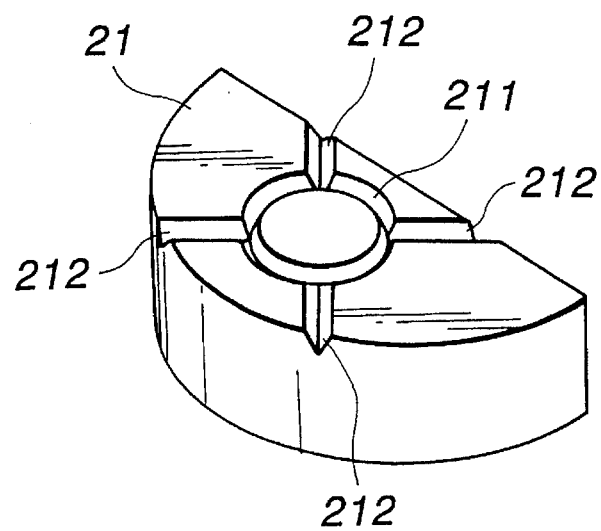
Figure 10:
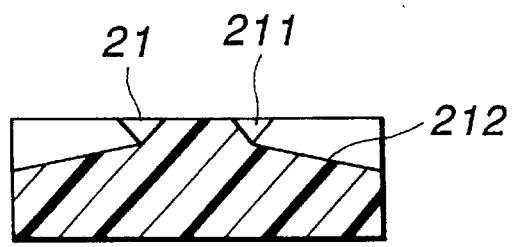

As shown in FIGS. 8 and 9, the dewatering means comprises a dewatering ditch 211 that is formed on the surface of the observation window 21 so as to lie outside the outer circumference of a coverable endoscope 4 and through which an objective lens 101 is visible, and branch ditches 212 extending straight from the dewatering ditch 211 toward the air nozzle 37a and water nozzle 37b which are surrounding the dewatering ditch 211 in the observation window 21.

Figure 11:
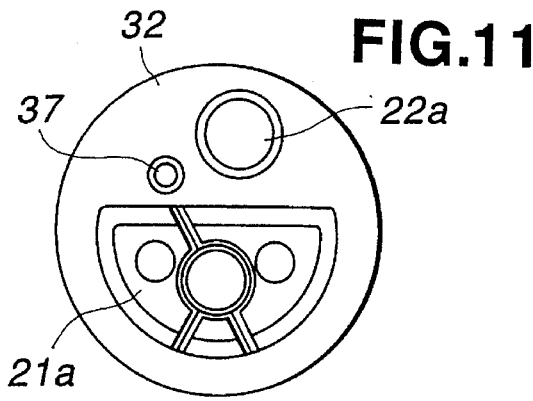

As shown in FIGS. 9 and 11, the cross section of each of the dewatering ditch 211 and branch ditches 212 formed on the observation window 21 is shaped substantially like a letter V. The branch ditches 212 are formed downslope so that the water in the dewatering ditch 211 will flow toward the ends of the observation window 21 smoothly. The other components are identical to those in the previous embodiment.

The operation of the observation window having the foregoing structure will be described.

In removal of dirt adhering to the surface of the observation window, first, water is supplied to the surface of the observation window through the water nozzle 37a of the distal structure 32. Next, air is supplied to the observation window through the air nozzle 37b in order to dewater the surface of the observation window 21. Water remaining on the surface of the observation window 21 is evacuated from the dewatering ditch 211 to the outside of the observation window via the branch ditches 212 by means of supplied air pressure.

Thus, the dewatering ditch 211 and branch ditches 212 are formed as a dewatering means on the surface of the observation window 21, which improves the dewatering efficiency concerning water remaining on the surface of the observation window. Eventually, endoscopic images output to the monitor via the observation optical system 100 become easy to see.

When an air/water nozzle 37 and a treatment adaptor outlet 22a alone are formed in the distal structure 32, a dewatering means is formed on the surface of an observation window 21a as shown in FIG. 11. Specifically, the dewatering means includes a dewatering ditch 211 and a branch ditch 212. Since the nozzle 37 is used to supply both air and water, only the branch ditch 212 is formed to head straight for the nozzle.

Figure 12:
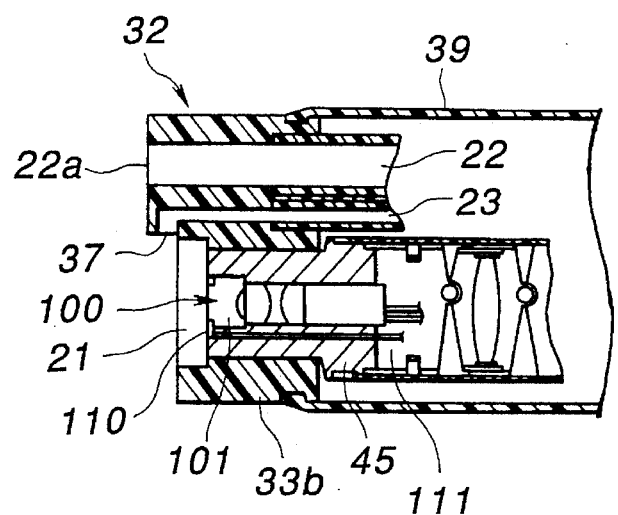
FIGS. 12 to 14 show the fourth embodiment of the present invention.
Figure 13:
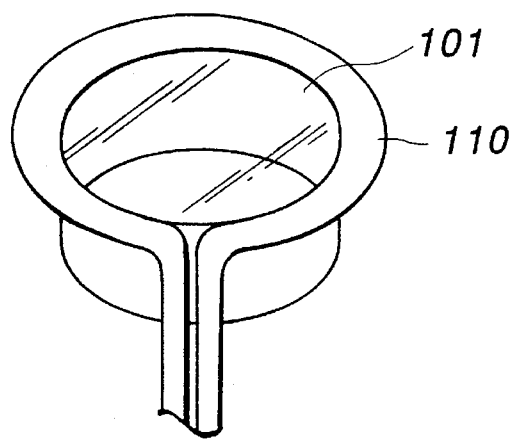
Figure 14:
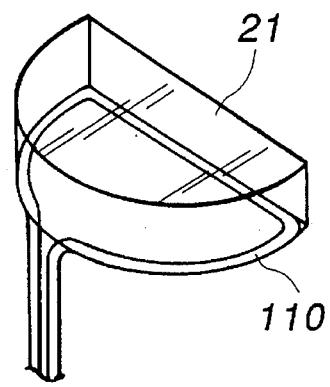

Referring to FIGS. 12 to 14, the fourth embodiment of the present invention will be described.

In this embodiment, an observation window heating means is formed to prevent or eliminate the cloud of an observation window 21.

As shown in FIGS. 12 and 13, a heating coil 110 is wound along the outer circumference of a lens 101 of an observation optical system 100, which is located in a distal part 45 of a coverable endoscope 4 fitted into an endoscope alignment hole 33b of an insertional part cover 3a, abutting on the observation window 21. The heating coil 110 is linked with a power supply cord 111 running through the distal part of the coverable endoscope 4. The power supply cord 111 lies through the insertional part cover 3a, operational part cover 3b, and universal cord cover 3c, and is connected to a temperature control unit, which is not shown, mounted in the light source apparatus and provided with a power supply function.

As mentioned above, the heating coil 110 is wound about the lens 101 in the coverable endoscope 4 inserted into the insertional part cover 3a. When the observation window 21 is heated by supplying power from an external unit, the cloud of the observation window 21 occurring during observation can be prevented or eliminated.

In FIG. 14, the heating coil 110 is wound along the outer circumference of the observation window 21, and linked with the power supply cord 111. The dewatering ditch 211 and branch ditch 212 on the observation window 21 are not illustrated.

Referring to FIGS. 15 to 18, the fifth embodiment of the present invention will be described.

Figure 15:
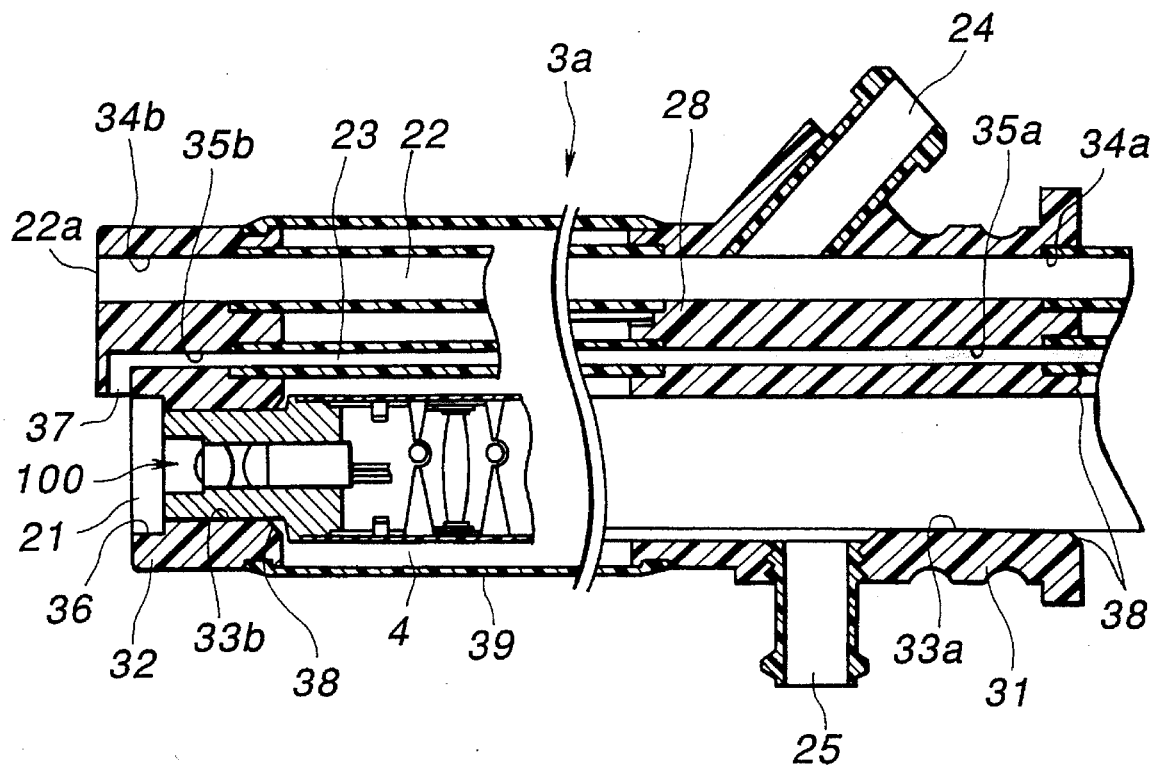
FIGS. 15 to 18 show the fifth embodiment of the present invention.

As shown in FIG. 15, a coverable endoscope insertion hole 33a formed to have a diameter permitting the tight fit of an insertional part 42 of a coverable endoscope 4, a forceps channel hole 34a also serving as a suction channel, and an air/water supply hole 35a are bored through a locking cap 31. A lens hole 36 in which an observation window 21 is locked, and an air/water nozzle 37 are formed on the distal surface of a distal structure 32. An endoscope alignment hole 33b formed to have a diameter permitting the tight fit of the insertional part 42 of the coverable endoscope 4, and a treatment adaptor channel hole 34b, and an air/water supply hole 35b are formed behind the distal surface of the distal structure 32.

Flexible tubes are used to link the treatment adaptor channel hole 34a and air/water supply hole 35a, which are lying through the locking cap 31, with the forceps channel hole 34b and air/water supply hole 35b, which are lying through the distal structure 32, thus forming a forceps channel 22 and an air/water channel 23. The channels extending from the locking cap 31 are linked with a fluid control apparatus 9.

A treatment adaptor insertion port 24 and a dilator tube cap 25 are projecting from the side of the locking cap 31.

Figure 16:
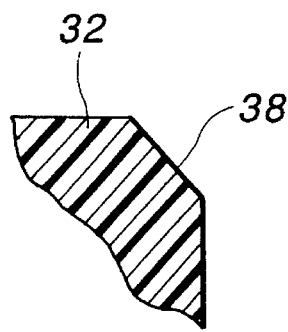
Figure 17:
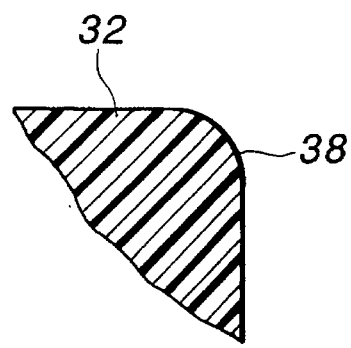

Guides 38 are formed on the insertional ends of the endoscope insertion hole 33a in the locking cap 31 and of the endoscope alignment hole 33b in the distal structure 32. As shown in FIGS. 16 and 17, the guides 38 are carved or rounded surfaces. The other components are identical to those in the previous embodiment.

As described above, the guides 38 are formed at the insertional ends of the endoscope insertion hole 33a formed in the locking cap 31 of the insertional part cover 3a, and of the endoscope alignment hole 33b formed in the distal structure 32, into both of which the coverable endoscope 4 is inserted. This greatly improves the smoothness in inserting the coverable endoscope 4 into the insertional part cover 3a.

Figure 18:
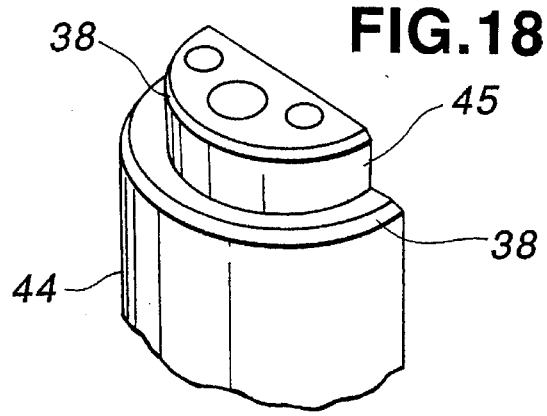

As shown in FIG. 18, the distal part 45 of the insertional part 42 of the coverable endoscope 4 may be provided with a guide 38 that is a carved or rounded surface as shown in FIGS. 16 and 17. This guide will prevent the distal part 45 of the coverable endoscope 4 from hooking on the inner circumferential surface of the locking cap 31 or distal structure 32. Thus, the insertional smoothness further improves.

The foregoing structures contribute to great reduction in occurrence of bending of the insertional part 42 of the coverable endoscope, damage to the observation optical system 100, or tearing of the insertional part cover 3a.

Figure 19:
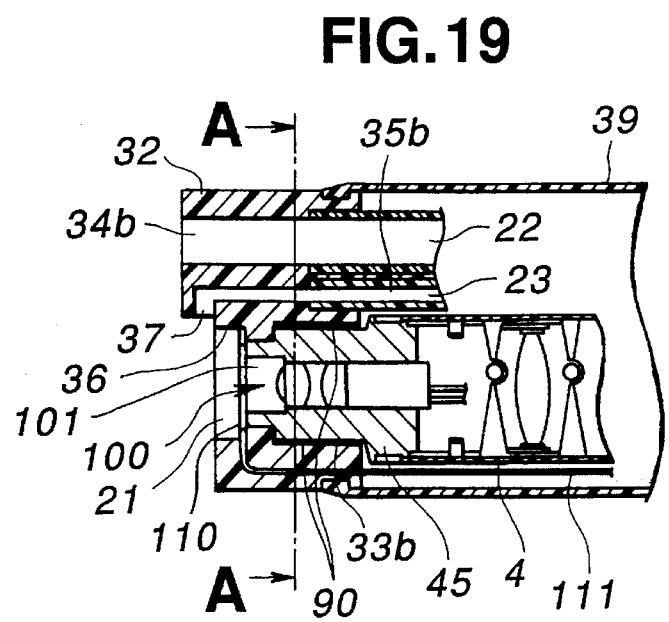
FIGS. 19 to 22 show the sixth embodiment of the present invention.
Figure 22:
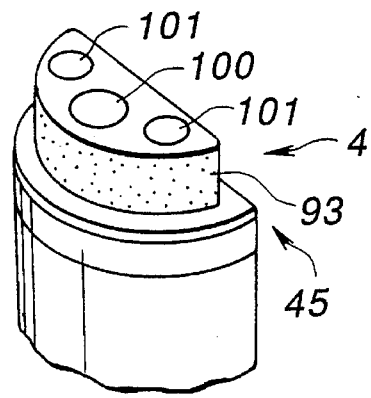

Referring to FIGS. 19 and 22, the sixth embodiment of the present invention will be described.

As shown in FIG. 19, an alignment holding means 90 is formed on a surface at which a coverable endoscope 4 and an endoscope alignment hole 33b meet, so that the coverable endoscope 4 will be tightly fitted into the endoscope alignment hole 33b.

Figures 20, 21:
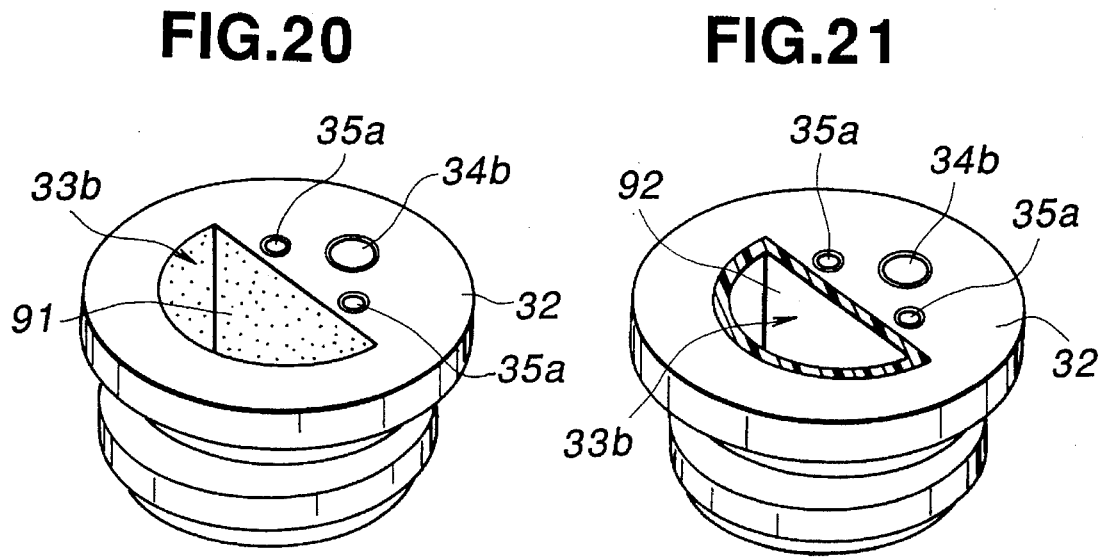

The alignment holding means 90 is realized, as shown in FIGS. 20 and 21, by forming a rough surface 91 as part of the inner circumferential surface of the endoscope alignment hole 33b in a distal structure 32 or by attaching an elastic member 92 to the inner circumferential surface thereof. When the elastic member 92 is attached to the distal structure 32 to realize the alignment holding means 90, the dimension of the endoscope alignment hole 33b of the coverable endoscope 4 is made smaller than the external dimension of a distal part 45 of a coverable endoscope 4, which is fitted into the endoscope alignment hole 33b, in consideration of the elasticity of the elastic member 92.

The operation of the alignment holding means having the above structure will be described.

The distal part 45 of the coverable endoscope 4 is fitted into the endoscope alignment hole 33b in the distal structure 32 of an insertional part cover 3a, and used for endoscopic examination. Since the inner circumference of the endoscope alignment hole 33b or the distal part 45 of the coverable endoscope 4 has the rough surface 91 or 93, or elastic member 92, the frictional resistance between the distal part 45 of the coverable endoscope 4 and the endoscope alignment hole 33b increases. This prevents the displacement of the coverable endoscope 4 fitted into the endoscope alignment hole 33b from occurring during bending.

As described above, the alignment holding means 90 is provided for a surface at which the distal part 4 of the coverable endoscope 4 and the endoscope alignment hole 33b meet, contributing to an increase in frictional resistance. This prevents the displacement of the coverable endoscope 4. Consequently, such a problem that illumination light emerging from the illumination optical system 101 placed in the coverable endoscope 4 does not irradiate a region to be observed precisely or that the field of view of the observation optical system 100 gets smaller can be resolved.

Furthermore, when realized with an elastic member 93, the distal structure 32 shown in FIG. 19 provides the same advantages as the alignment holding means 90 shown in FIG. 21.

Referring to FIGS. 23 to 28, the seventh embodiment of the present invention will be described.

Figure 23:
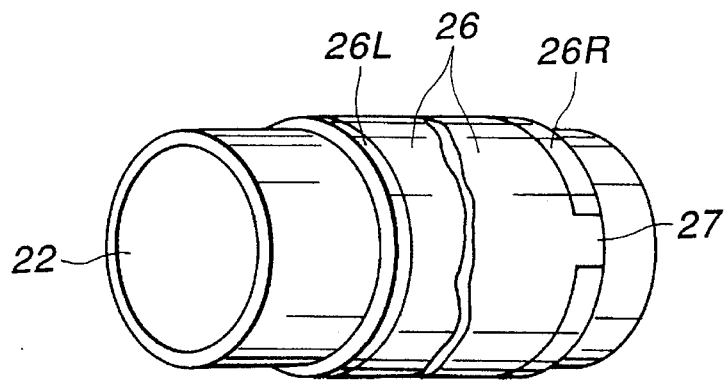
FIGS. 23 to 28 show the seventh embodiment of the present invention.

As shown in FIG. 23, the outer surface of a flexible treatment adaptor channel 22 is coated with metallic foil 26 made of a conducting film material such as stainless steel. In addition, insulating bands 26R and 26L made of an insulating resin are wound about the right and left ends of the metallic foil 26. Either of the two insulating bands 26R and 26L lying right and left, for example, the insulating band 26R is provided with a conducting terminal 27 that is an extension of the end of tile metallic foil 26.

Figure 24:
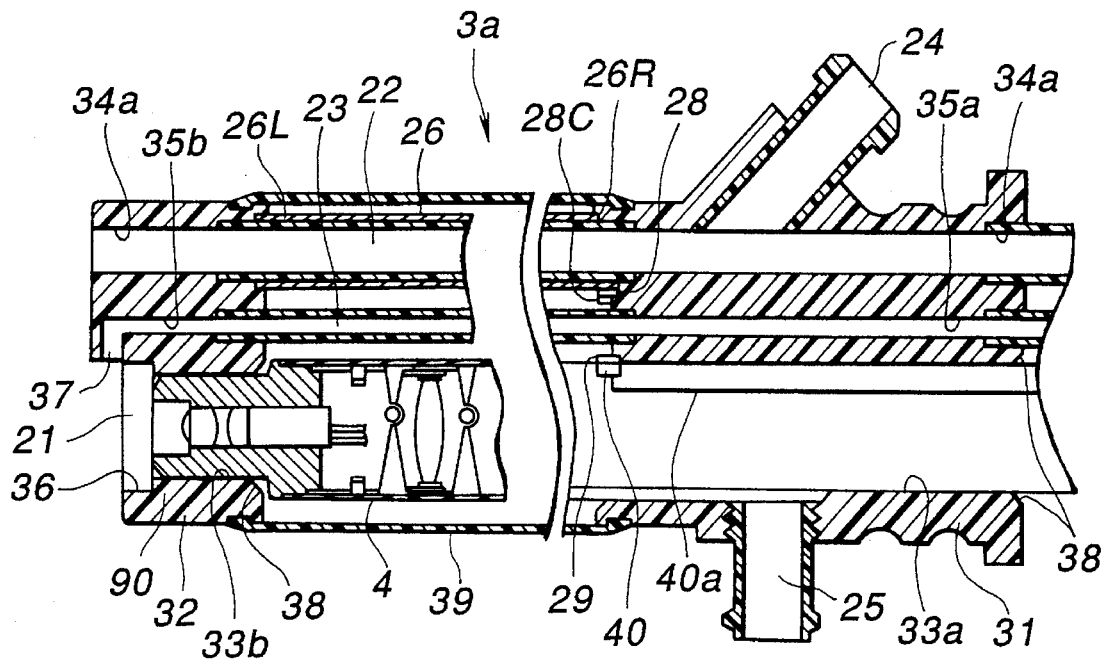

The treatment adaptor channel 22 having the foregoing structure is placed as shown in FIG. 24 to constitute an insertional part cover 3a. At this time, the insulating band 26L of the treatment adaptor channel 22 is facing a distal structure. The conducting terminal 27 formed on the insulating band 26R is electrically coupled with a terminal electrode plate 28a of a terminal 28 that is electrically isolated from a locking cap 31. The conducting terminal 27 is also connected to a terminal 29, which is linked with a conducting cord 28c extending from the terminal electrode plate 28a, electrically isolated from the locking cap 32, and formed similarly to the terminal 28 lying in the endoscope insertion hole 33a.

Figures 25, 26:
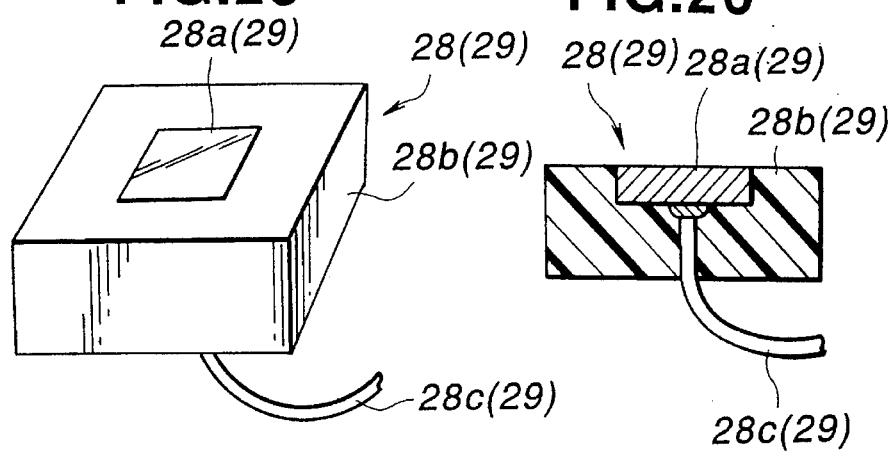

The terminal 28 or 29 is made, as shown in FIGS. 25 and 26, by embedding the terminal electrode plate 28a or 29a in a frame 28b or 29b made of a resin having an insulating property. The conducting cord 28c or 29c is extending from the terminal electrode plate 28a or 29a.

The operation of the insertional part cover 3a having the aforesaid structure will be described.

When a coverable endoscope 4 is fixed at a specified position, the terminal 29 comes into contact with a ground terminal 40 formed on the coverable endoscope 4. With the contact of the terminal 29 with the ground terminal 40, the metallic foil 26 coated over the outer surface of a forceps channel 22 is connected to a ground plug via the conducting terminal 27, terminal 28, conducting cord 28c, terminal 29, ground terminal 40, and ground cord 40a.

In this state, when, for example, a high-frequency treatment adaptor is inserted into the treatment adaptor channel 22, if high-frequency power is applied, high-frequency noises may be generated by the high-frequency treatment adaptor. The high-frequency noises are attenuated through the ground plug.

Since the treatment adaptor channel 22 is provided with a shielding means as described above, even when the coverable endoscope 4 is tightly fitted into the insertional part cover 3a in order to use a high-frequency treatment adaptor, influence of high-frequency noises will not extend to an imaging device. Consequently, adequate treatment can be given under the observation of easy-to-see endoscopic images.

The ground plug is placed in, for example, a light source apparatus 7.

Figure 27:
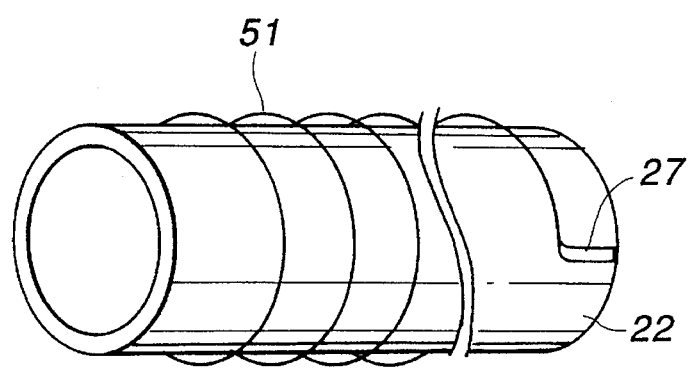
Figure 28:
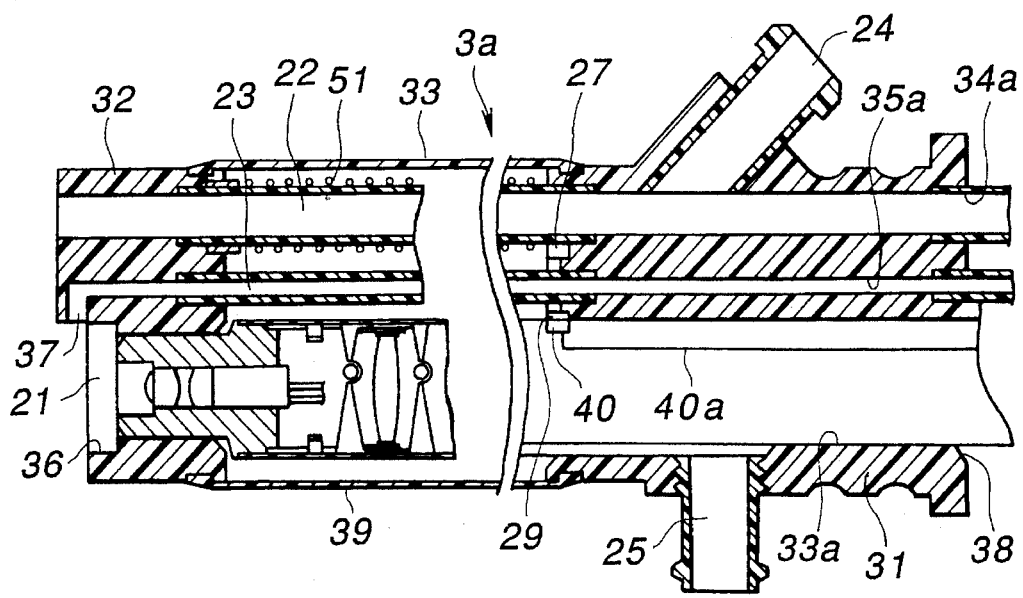

In FIG. 27, a coil 51 made of a conducting material may be wound about the treatment adaptor channel 22 instead of the metallic foil 26 coated over the outer circumference of the treatment adaptor channel 22. The coil 51 is connected and grounded similarly to the metallic loll 26 in the previous embodiment shown in FIG. 28. This variant also provides the same operation and advantages as the previous embodiment.

Figure 29:
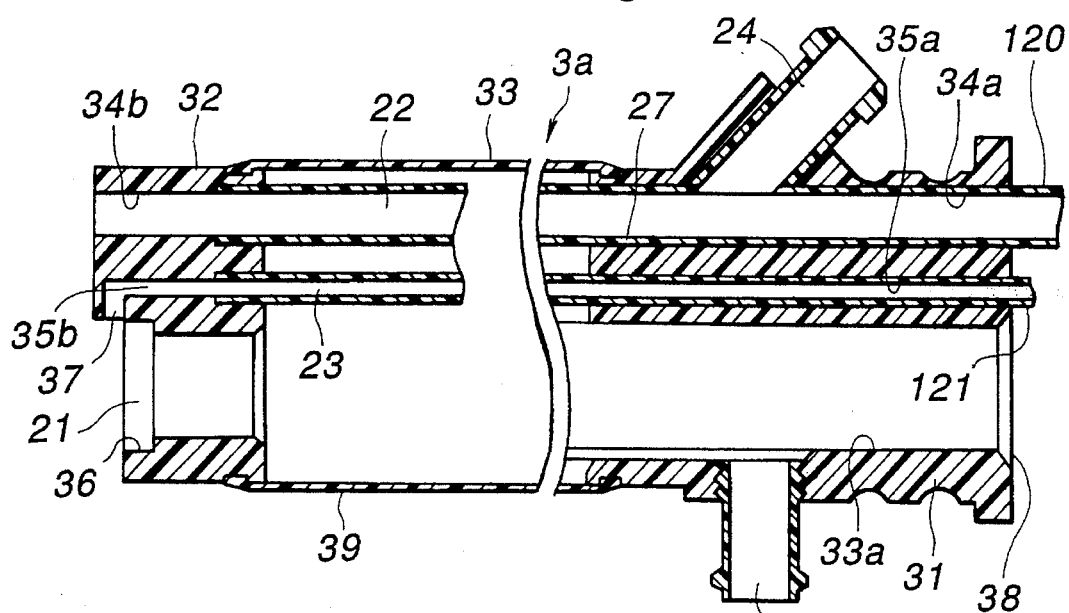
FIG. 29 shows the eighth embodiment of the present invention and is a cross-sectional view showing a structure of an insertional part cover.

Referring to FIG. 29, the eighth embodiment of the present invention will be described.

In FIG. 29, flexible tubes 120 and 121 are attached to a suction/treatment adaptor channel hole 34a and an air/water supply hole 35a which are formed in a locking cap. One ends of the tubes 120 and 121 join a treatment channel hole 34b and an air/water supply hole 35b which are formed in a distal structure, thus forming a suction channel 22 and an air/water supply channel 23. The other ends of the tubes 120 and 121 are directly connected to a fluid control apparatus 9. That is to say, the suction channel (treatment channel) 22 and air/water supply channel 23 are formed to have joints in the middles of the tubes 120 and 121.

In short, the tubes 120 and 121 extending from the fluid control apparatus 9 are directly joined with the air/water supply hole 35b and treatment channel hole 34 which are formed in the distal structure 32, thus forming the air/water supply channel 23 and suction channel 22. Therefore, when fluid is caused to flow through either of the channels, turbulence in an air or water flow, which has occurred at a joint between pipes, does not occur. This means that an air/water supply capacity will not deteriorate during examination or treatment.

A problem concerning dewatering efficiency at a joint between pipes will also be resolved. Furthermore, since the number of joints decreases, labor and costs required for manufacturing a cover can be saved.

Figure 30:
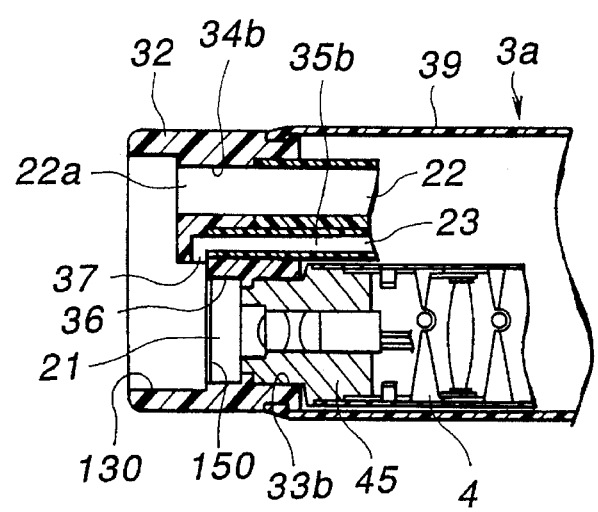
FIGS. 30 and 31 show the ninth embodiment.
Figure 31:
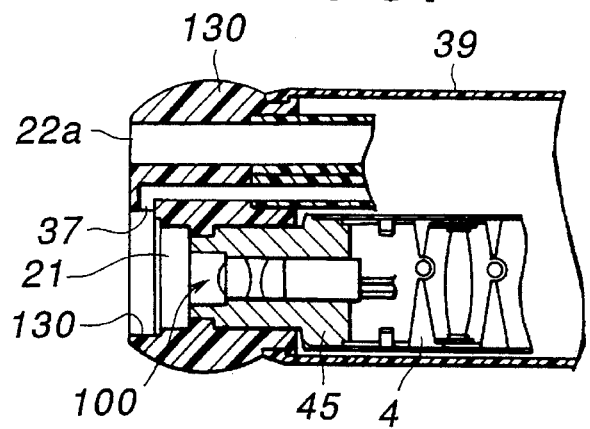

Referring to FIGS. 30 and 31, the ninth embodiment will be described.

In FIG. 30, a distal structure 32 has a cuff 130 for providing a certain distance from an observation window 21 formed in a distal endoscope part 45 to a subject to be observed.

The presence of the cuff 130 in the distal structure 32 prevents the observation window 21 from coming into direct contact with a body cavity. Since a distance to a subject to be observed can be reserved reliably, observation performance improves.

In FIG. 31, the cuff 130 of the distal structure 32 is streamlined so that the center of the distal structure will have a larger external diameter than the distal end of the distal structure.

When the distal structure 32 is formed as described above, an insertional cover 3a can be inserted smoothly and inserted toward a stenotic region smoothly.

In this embodiment, a streamlined cross section is presented as other example. The cross-sectional shape of the distal structure 32 is not limited to the streamlined shape. When the insertional part cover 3a is made available in various shapes in conformity with regions to be observed, the cover 3 can be used in more selective manner.

Figure 32:
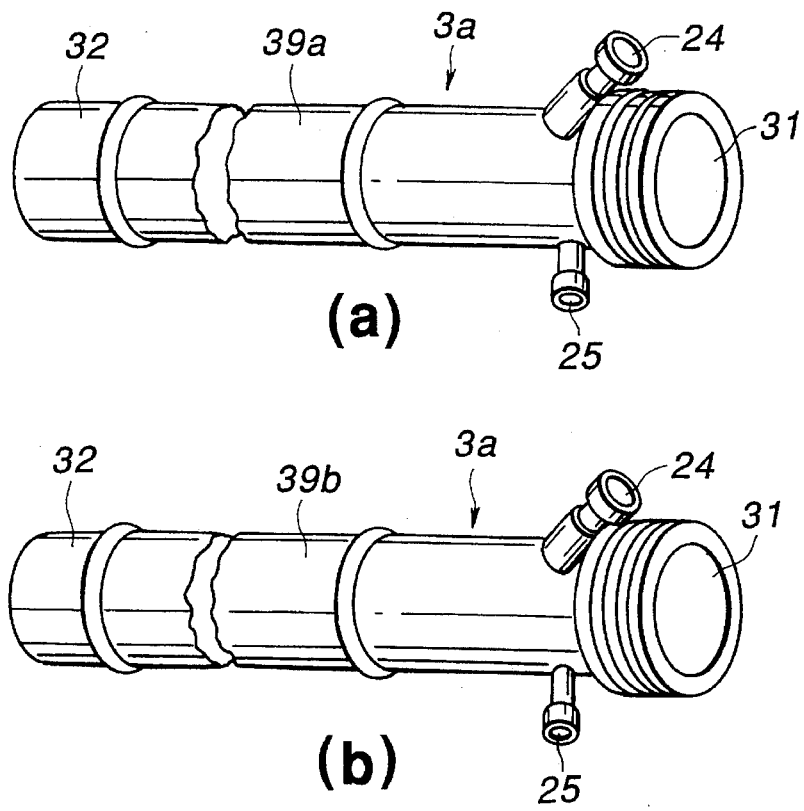
FIG. 32(*a*) and 32(*b*) show the tenth embodiment of the present invention, explaining different component members for an insertional part cover.

Referring to FIG. 32, the tenth embodiment of the present invention will be described.

As long as the structure of an insertional part cover 3a is unchanged, the same member is usually employed as a cover skin 39 of the insertional part cover 3a used in a covered endoscope system i. In other words, the insertional part cover 3a always consists of the same components as long as the structure is unchanged.

In FIGS. 32(a) and 32(b), the insertional part cover 3a has the same structure but is different in hardness of a cover skin. Specifically, the insertional part cover 3a shown in FIG. 32a is formed by coupling a distal structure 32 with a locking cap 31 using a high-flexibility cover skin 39a. The insertional part cover 3a shown in FIG. 32b is formed by coupling the distal structure 32 with the locking cap 31 using a low-flexibility cover skin 39b.

As described above, when the cover skins 39a and 39b having the same structure but different flexibilities are used to form the insertional part cover 3a, the insertional part cover 3a can be used selectively according to an observer's purpose of examination or likes.

Not only the flexibility of the cover skin 39 is varied but also the elasticity or surface roughness thereof may be varied.

Furthermore, the insertional part covers 3a may be made available in different types depending on the inner diameter of a forceps channel 22 so as to be used selectively.

Referring to FIGS. 33 to 36, the eleventh embodiment of the present invention will be described.

Figure 33:
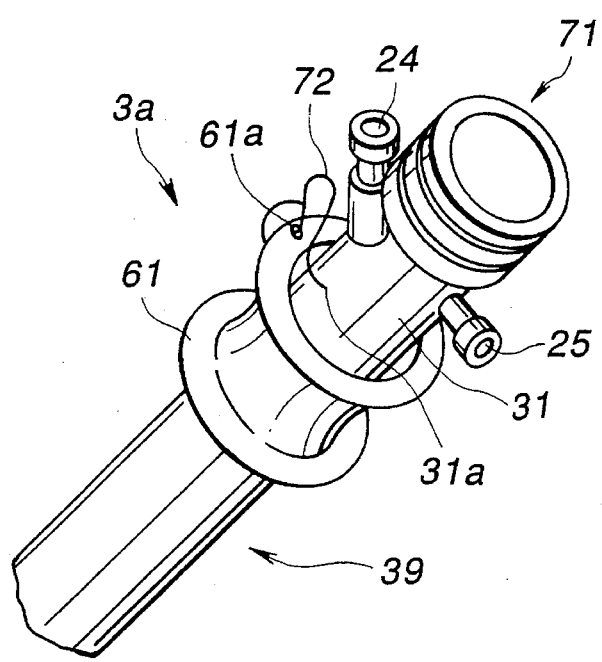
FIGS. 33 to 36 show the eleventh embodiment of the present invention.

When a covered endoscope system is used for examination, covers for shielding the outer surface thereof; such as, an insertional part cover 3a, an operational part cover 3b, and a universal cord cover 3c are included as components of the system. A mouthpiece, which must definitely be disinfected before every examination, is not included as one component of a covered endoscope system. In FIG. 33, a mouthpiece 61 is united with a locking cap 31 of the insertional part cover 3a so as to be detachable.

As shown in FIG. 33, a locking cap 31 of the insertional part cover 3a and the mouthpiece 61 are coupled with each other using an attachment thread 72, thus forming a mouthpiece-united insertional part cover 71.

To be more specific, as shown in FIG. 33, the mouthpiece 61 is put on the locking cap 31, the attachment thread 72 is run through a thread hole 31a bored on the locking cap 31 and a thread hole 61a bored on the mouthpiece 61, and thus the mouthpiece-united insertional part cover 71 is formed.

The operation of the mouthpiece-united insertional part cover 71 having the above structure will be described.

When the mouthpiece-united insertional part cover 71, in which the mouthpiece 61 and locking cap 31 are united with each other using the attachment thread 72, is used for endoscopic examination, the attachment thread 72 for united connection is cut out to separate the mouthpiece 61 from the locking cap 31. The mouthpiece 61 is then applied to a patient.

Since the mouthpiece 61 is united with the insertional part cover 3a as described above, the mouthpiece 61 which has been disinfected reliably can be put to use.

Figure 34:
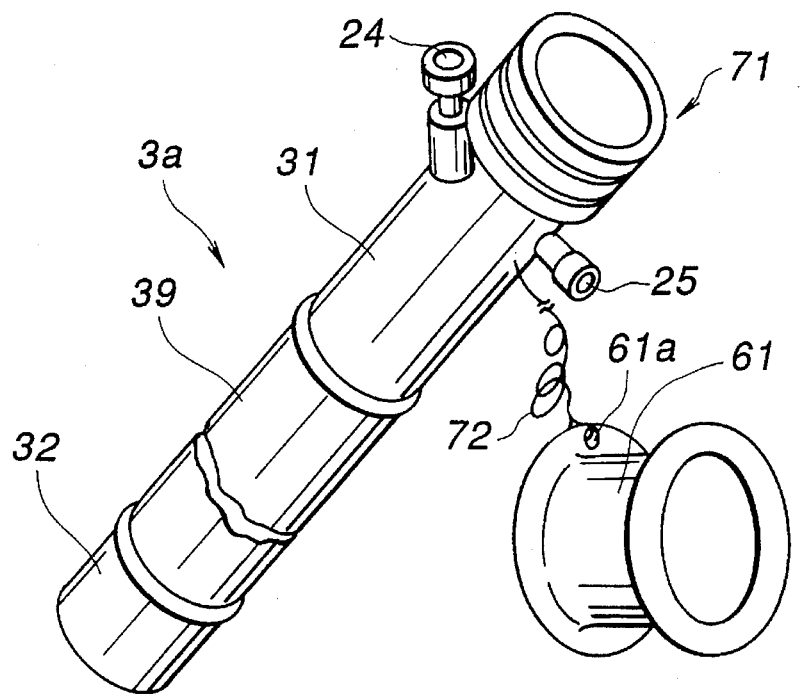

In FIG. 34, the mouthpiece 61 is not put on the insertional part cover 3a. The insertional part cover 3a and mouthpiece 61 are united with each other using the attachment tread 72 similarly to the foregoing embodiment. The attachment thread 72 is long enough to reach a distal structure 32 formed at the distal end of the insertional part cover 3a. The attachment thread 72 need not be cut out before use. The other components, operation, and advantages are identical to those of the previous embodiment.

Figure 35:
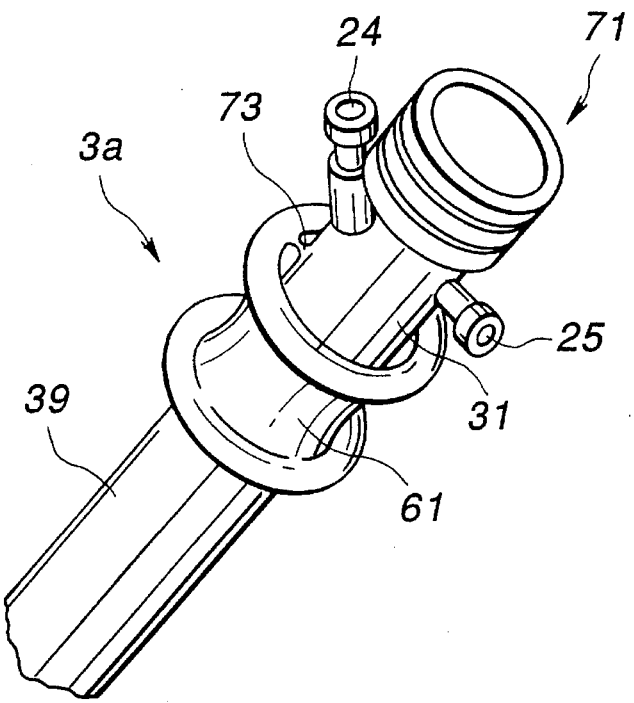
Figure 36:
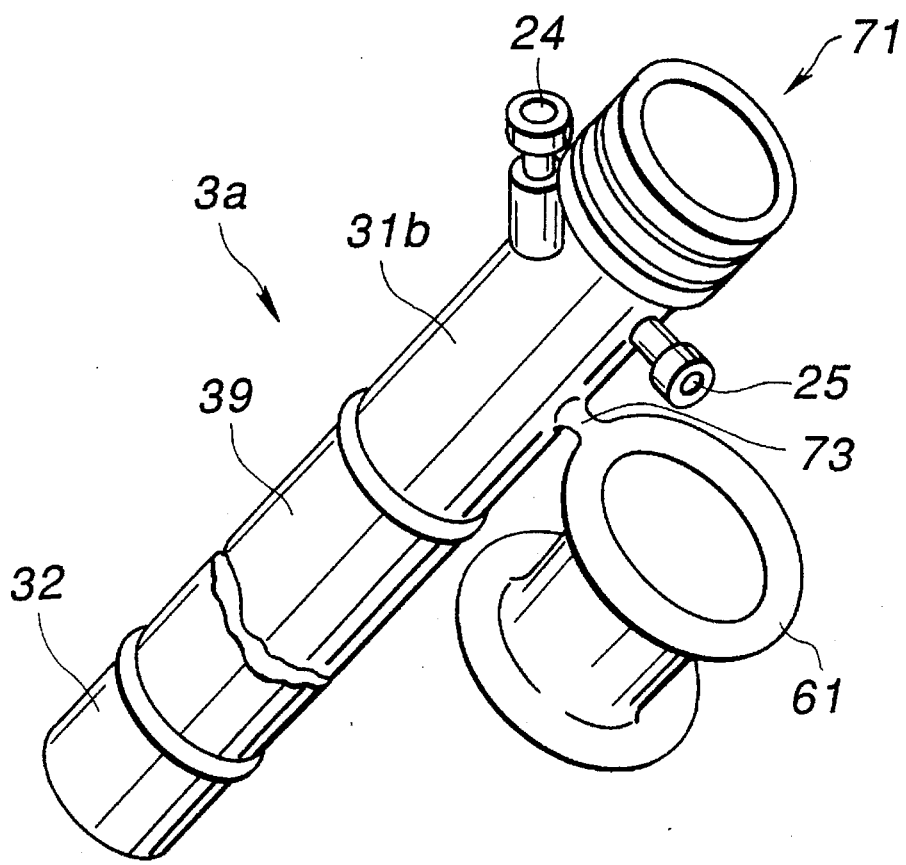

In FIGS. 35 and 36, the mouthpiece 61 and the locking cap 31 are molded as a united body, thus forming the mouthpiece-united insertional part cover 71.

The mouthpiece-united insertional part cover 71 shown in FIG. 35 has a rib for coupling the inner circumferential surface of the mouthpiece 61 with the outer circumferential surface of the locking cap 31, which is a mold. The mouthpiece-united insertional part cover 71 shown in FIG. 36 has a rib for coupling the outer circumferential surface of the mouthpiece 61 with the outer circumferential surface of the locking cap 31, which is a mold.

When the mouthpiece 61 and locking cap 31 are molded as a united body, the work for attaching the mouthpiece 61 to the insertional part cover 3a can be omitted. For use in examination, first, the mouthpiece 61 is put on the locking cap 31. The other operation and advantages are identical to those in the previous embodiment.

Figure 37:
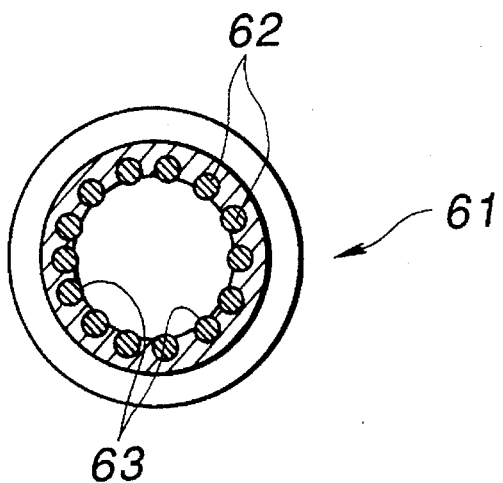
FIGS. 37 and 38 show the eleventh embodiment of the present invention.
Figure 38:
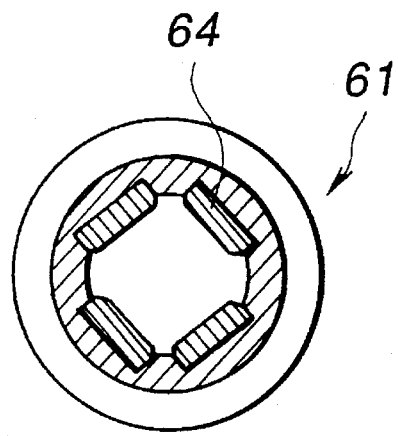

Referring to FIGS. 37 and 38, the eleventh embodiment of the present invention will be described.

A mouthpiece employed for endoscopic examination has a smooth internal surface so that an insertional part of an endoscope moves smoothly along the inner circumferential surface of the mouthpiece 61 when inserted into the mouthpiece 61. However, when the mouthpiece is used in conjunction with a covered endoscope system, there is a fear that a thin cover skin of an insertional part cover of a covered endoscope may be hooked and torn.

In FIG. 37, multiple ball-fit holes 62 are bored on the inner circumferential surface of a mouthpiece 61 made of a resin. Balls 63 made of a metal or a resin are fitted into the holes so as to be rotatable. Thus, a mouthpiece is formed.

When an endoscope is inserted into the mouthpiece 61 having the foregoing structure, since the rotatable bails 63 are resting on the inner circumferential surface of the mouthpiece 61 and serve as a rolling means, an insertional part cover 3a into which a coverable endoscope 4 is fitted tightly abuts on the rotating balls 63 and passes through the mouthpiece 61. This results in reduced frictional resistance.

As described above, the rotatable bails 63 resting on the inner circumferential surface of the mouthpiece and serving as a rolling means enables smooth insertion of the insertional part cover 3a, with which the coverable endoscope 4 is sheathed, into a body cavity. The frictional resistance occurring between the inner circumferential surface of the mouthpiece 61 and the insertional part cover is so small that occurrence of tear of a cover skin 39 during insertion can be minimized.

Instead of the rotating balls 63, rollers 64 each of which is, as shown in FIG. 38, formed so as to be rotatable and has a cylindrical cross section may be used as the rolling means. This variant will also provide the same advantages as the foregoing embodiment.

In the present invention, it will be apparent that a wide range of embodiments can be formed on the basis of the present invention without departing from the spirit and scope of the invention. The invention will be limited to the appended claims but not restricted to any specified embodiments.

What is claimed is:

1. A covered endoscope system, comprising:

a cover;

a coverable endoscope to be inserted into said cover for use; and an alignment holding means extends around the entire inner surface of a distal end portion of said cover wherein said alignment holding means holds together said cover and said coverable endoscope by providing a frictional fit between a substantially large area of the external surface of a distal end portion of said coverable endoscope and a substantially large area of the inner surface of a distal end portion of said cover.

2. A covered endoscope system according to claim 1, wherein said alignment holding means is a rough surface formed as part of the inner surface of said endoscope alignment hole.

3. A covered endoscope system according to claim 1, wherein said alignment holding means is a rough surface formed as part of the outer surface of said distal part of said coverable endoscope.

4. A covered endoscope system according to claim 1, wherein said alignment holding means is an elastic member lining the inner surface of an endoscope alignment hole formed in said distal end portion of said cover.

\* \* \* \* \*